United States Patent [19]

Rutledge

[11] 4,147,663

[45] Apr. 3, 1979

[54] OXIDATIVE COUPLING OF ALKYLPHENOLS, ALKOXYPHENOLS AND NAPHTHOLS CATALYZED BY METAL COMPLEXES OF AMINO CARBOXYLIC AND AMINO SULFONIC ACIDS

[75] Inventor: Thomas F. Rutledge, Wilmington, Del.

[73] Assignee: ICI Americas Inc., Wilmington, Del.

[21] Appl. No.: 846,812

[22] Filed: Oct. 31, 1977

Related U.S. Application Data

[60] Division of Ser. No. 666,228, Mar. 12, 1976, Pat. No. 4,067,890, which is a continuation-in-part of Ser. No. 550,860, Feb. 18, 1975, abandoned, which is a continuation-in-part of Ser. No. 500,210, Aug. 23, 1974, abandoned.

[51] Int. Cl.$^2$ .................. B01J 31/04; B01J 31/22; B01J 31/26
[52] U.S. Cl. .................. 252/428; 252/430; 252/431 C; 252/431 N
[58] Field of Search ............... 260/396 N, 613 R, 620, 260/47 ET, 619 B, 619 F; 252/428, 430

[56] References Cited

U.S. PATENT DOCUMENTS

| | | | |
|---|---|---|---|
| 3,213,114 | 10/1965 | Braxton et al. | 260/396 R |
| 3,219,625 | 11/1965 | Blanchard et al. | 260/396 N X |
| 3,219,626 | 11/1965 | Blanchard et al. | 260/395 N X |
| 3,306,874 | 2/1967 | Hay | 260/396 N X |
| 3,536,774 | 10/1970 | Itoi et al. | 252/428 X |
| 4,070,383 | 1/1978 | Rutledge | 252/430 X |

*Primary Examiner*—Patrick Garvin

[57] ABSTRACT

Self-condensation products obtained by the oxidative coupling of certain alkylphenols, alkoxyphenols or naphthols are prepared by contacting an aqueous mixture of the phenol or naphthol with oxygen in the presence of a metal complex of an aminocarboxylic acid or an aminosulfonic acid.

5 Claims, No Drawings

OXIDATIVE COUPLING OF ALKYLPHENOLS, ALKOXYPHENOLS AND NAPHTHOLS CATALYZED BY METAL COMPLEXES OF AMINO CARBOXYLIC AND AMINO SULFONIC ACIDS

BACKGROUND OF THE INVENTION

This application is a division of application Ser. No. 666,228, filed Mar. 12, 1976 and now U.S. Pat. No. 4,067,890, which was a continuation-in-part of application Ser. No. 550,860 filed Feb. 18, 1975, now abandoned which was a continuation-in-part of application Ser. No. 500,210 filed Aug. 23, 1974 now abandoned.

FIELD OF THE INVENTION

The present invention relates generally to an improved process for preparing self-condensation products, such as diphenoquinones and biphenols, from alkylphenols and alkoxyphenols, and dinaphthenoquinones and binaphthols from naphthols, and to a catalyst for use in said process. More particularly, the invention relates to the preparation of condensation products of alkyl- and alkoxy- phenols, 1-naphthol and substituted 1-naphthols by contacting an aqueous mixture of the phenol or naphthol with oxygen or an oxygen-containing gas in the presence of a metal complex of an aminocarboxylic acid or an aminosulfonic acid.

DESCRIPTION OF THE PRIOR ART

It is well known in the art that substituted phenols can be oxidized to yield self-condensation products, including diphenoquinones, biphenols and polyphenoxy ethers. The procedure employed in the preparation of these derivatives is generally referred to as the oxidative coupling of phenols.

The self-condensation products resulting from these oxidative coupling reactions can be categorized as either the result of carbon-carbon or carbon-oxygen coupling of said phenols. Diphenoquinones and biphenols are prepared by carbon-carbon coupling in accordance with the following general reactions depending upon the reactive sites available in the phenol employed.

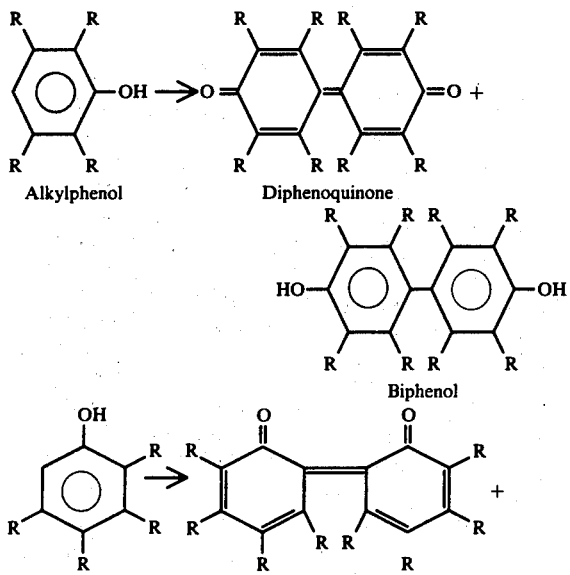

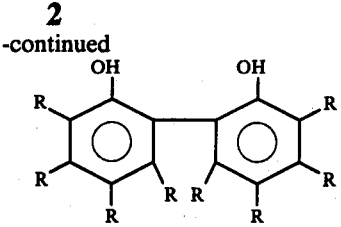

wherein R is either hydrogen, alkyl, alkoxy, or another substituent known in the art.

Similarly, polyphenoxy ethers are prepared by carbon-oxygen coupling in accordance with reactions such as the following general reaction:

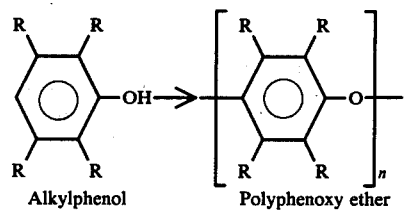

wherein R is as defined above and n is an integer.

A variety of materials, including metals and various salts and complexes thereof, have previously been disclosed as useful in promoting the oxidative coupling of alkylphenols. Thus, U.S. Pat. No. 2,785,188 issued to Coe, discloses that copper powder may be utilized to prepare diphenoquinones from 2,6-dialkyl-4-halophenols. Similarly, various copper salts and combinations or complexes prepared from copper salts and a variety of nitrogen-containing compounds have been disclosed as useful in the preparation of both diphenoquinones and polyphenoxy ethers. These include, for example, cupric salts of primary and secondary amines (U.S. Pat. Nos. 3,306,874 issued to Hay); cupric salts of tertiary amines (3,306,875 issued to Hay and 3,134,753 issued to Kwiatek); cupric complexes of pyridine (3,219,625 and 3,219,626 both of which were issued to Blanchard et al.) and a mixture of a cupric halide or a cupric carboxylate and a tertiary amine (3,384,619). Additional catalysts prepared from cuprous or cupric salts and amines have been disclosed as, for example, in 3,544,516; 3,639,656; 3,642,699 and 3,661,848, all of which were issued to Bennett and Cooper. Finally, 3,210,384 issued to Hay discloses the use of complexes of a basic cupric salt and a nitrile or tertiary amide and 3,549,670 issued to Spousta et al. describes the use of a copper or copper alloy catalyst and a nitrogen base. The use of cupric salts of carboxylic acids as the oxidizing agent in an oxidative coupling reaction is also disclosed in the art. See, in this regard, 3,247,262 issued to Kaeding.

The use of manganese and cobalt compounds has also been disclosed in U.S. Pat. Nos. 3,337,501 issued to Bussink et al. and 3,573,257 issued to Nakashu et al.

A variety of basic compounds have also been employed in oxidative coupling reactions. In many of these systems, such as those disclosed in U.S. Pat. Nos. 2,905,674 issued to Folbey and in 2,785,188 issued to Coe, the function of the alkaline material was to react with an acidic component, such as HCl, liberated during the course of the reaction and, therefore, a stoichiometric amount of the base was used.

However, there is no disclosure or suggestion in the prior art that metal complexes of aminocarboxylic or aminosulfonic acids would be useful in these oxidative coupling reactions.

It should also be noted that all of the previous methods of preparing coupled products of alkyl or alkoxy substituted phenols or naphthols have required the use of either organic solvents or stoichiometric amounts of the organic reagents. There has not previously been available a catalyst system useful in the preparation of carbon-carbon coupled phenols and naphthols in an aqueous reaction medium. Also, with most of the prior art systems the resulting product or products were determined by the particular catalyst employed and could not easily be controlled. Thus, there has not been available a system which could be modified to produce either the biphenol or diphenoquinone derivative, the stilbene quinone or bisphenol or the dinaphthenoquinone or binaphthol directly from the reaction mixture.

In accordance with the present invention, it has been found that certain substituted phenols, 1-naphthol and substituted 1-naphthol may be oxidatively coupled in an aqueous medium if there is employed a catalytic amount of a metal complex of an aminocarboxylic acid or an aminosulfonic acid. Further improvements have been discovered when an alkaline material is included with the metal complex. For example, it has been found that the type of product which is produced can be controlled by the amount of metal complex or alkaline material employed in the process. By comparison, the prior art processes have a number of disadvantages which have restricted their utility. These include (a) the requirement that the reaction be conducted in an organic solvent, (b) the fact that the primary product produced is often the polyphenoxy ether, and (c) the inability to form the biphenol, bisphenol or binaphthol derivative directly without requiring that this material be produced by a subsequent hydrogenation of the diphenoquinone, stilbene quinone or dinaphthenoquinone respectfully, prepared in the oxidative coupling reaction.

SUMMARY OF THE INVENTION

In accordance with the present invention it has been found that the use of a catalytic amount of a metal complex of an aminocarboxylic acid or an aminosulfonic acid as is hereinafter defined results in an improved process for the preparation of carbon-carbon coupled products of alkylphenols, alkoxyphenols or 1-naphthols via the oxidative coupling of said phenols or naphthols.

DESCRIPTION OF THE PREFERRED EMBODIMENTS

As mentioned above, in accordance with the present invention condensation products resulting from the oxidative coupling of phenols and naphthols are prepared, in an aqueous medium, by contacting an aqueous solution of the phenol or naphthol with oxygen or an oxygen-containing gas in the presence of a metal complex of an amino-carboxylic acid or an aminosulfonic acid. The phenols or naphthols and metal complexes which may be utilized are critical to the present invention and are described in detail below.

Phenols/Naphthols

The phenols which may be employed in carrying out the present invention include both alkylphenols and alkoxyphenols. The specific phenols which may be utilized are described in detail below.

The first type of alkylphenols which may be utilized are defined as any alkylphenol having at least two alkyl substituents and only one unsubstituted position ortho or para to the hydroxyl group. In other words, the phenols must have at least two alkyl substituents and the substituents must be in the ortho, ortho (2,6 in the formula below) or ortho, para (2,4 in the formula below) positions. These phenols are frequently referred to by the position of the alkyl substituent or substituents on the benzene ring as set forth in the following formula:

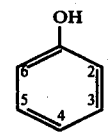

However, in the process of the present invention, when an ortho, para substituted phenol is used, at least one of the alkyl groups in the ortho (2) or para (4) position must be a tertiary alkyl and when an ortho (2), ortho (6) substituted phenol is used only one of the ortho substituents may be a tertiary alkyl. In addition to dialkylphenols, tri- and tetra- substituted materials may also be utilized provided that the substituents in the ortho and/or para positions satisfy the criteria set forth above.

Thus, the alkylphenols will have one of the following formulas:

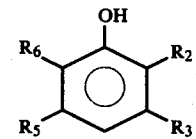

wherein $R_2$ and $R_6$ are alkyl groups containing from 1 to about 12 carbon atoms, provided that only one of said alkyl groups may be a tertiary alkyl, and $R_3$ and $R_5$ are hydrogen or alkyl groups containing from 1 to about 12 carbon atoms provided that if both $R_3$ and $R_5$ are alkyl only one of said alkyl groups may be a tertiary alkyl.

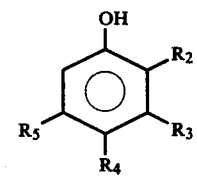

wherein $R_2$ and $R_4$ are alkyl groups containing from 1 to about 12 carbon atoms, provided that at least one of said alkyl groups is a tertiary alkyl and $R_3$ and $R_5$ are hydrogen or alkyl.

As used herein, the term alkyl refers to any monovalent radical derived from a saturated aliphatic hydrocarbon by removal of one hydrogen atom therefrom. The term includes both straight chain and branched chain materials containing from 1 to about 12 carbon atoms. Preferred results are achieved with alkylphenols wherein the alkyl substituent contains from 1 to about 5 carbon atoms.

The alkyl substituents are referred to herein as primary, secondary or tertiary alkyl depending upon the greatest number of carbon atoms attached to any single carbon atom in the chain. Thus, a primary alkyl has up to 1 carbon atom attached to any single carbon atom as in methyl, ethyl, n-propyl and n-butyl. A secondary alkyl has two carbon atoms attached to a single carbon atom as in isopropyl, isobutyl and secondarybutyl. A tertiary alkyl has three carbon atoms attached to a single carbon atom as in tertiarybutyl.

Condensation products of any alkylphenol coming within the above-mentioned definition may be prepared in accordance with the present invention. As is apparent from that definition, the alkylphenols include dialkylphenols, trialkylphenols, and tetraalkylphenols. Specifically, the phenols which may be utilized include the following:

ortho, para substituted phenols including 2,4-dialkylphenols, 2,3,4 trialkylphenols, 2,4,5 trialkylphenols, and 2,3,4,5 tetraalkylphenols wherein the alkyl groups are either methyl or a primary, secondary, or tertiary alkyl provided that at least one of the alkyl groups in either the 2 or the 4 position is a tertiary alkyl, and ortho, ortho substituted phenols including 2,6-dialkylphenols, 2,3,6 trialkylphenols and 2,3,5,6 tetraalkylphenols wherein the alkyl groups are either methyl or a primary, secondary, or tertiary alkyl provided that at least one of the alkyl groups in either the 2 or the 6 position is either a primary or secondary alkyl.

Representative ortho, para substituted phenols which may be used include, for example, 2,4-ditertiarybutylphenol, 2-methyl-4-tertiarybutylphenol, 2-tertiarybutyl-4-methylphenol, 2,4-ditertiaryamylphenol, 2,4-ditertiaryhexylphenol, 2-isopropyl-4-tertiarybutylphenol, 2-secondarybutyl-4-tertiarybutylphenol, 2-tertiarybutyl-3-ethyl-4-methylphenol, 2-octyl-3-dodecyl-4-tertiarybutylphenol, 2,5-dimethyl-4-tertiarybutylphenol, 2-tertiarybutyl-4,5 dioctylphenol and 2-methyl-3-ethyl-4-tertiarybutyl-5-nonylphenol.

Representative 2,6-dialkylphenols (ortho, ortho substituted) include, for example, 2,6-xylenol, 2-methyl-6-butylphenol, 2,6-diisobutyl phenol, 2-octyl-6-methyl phenol, 2-isobutyl-6-dodecyl phenol, 2-ethyl-6-methyl phenol, 2,6-dodecyl phenol, 2-methyl-6-tertiary-butyl phenol, 2,6-diisopropyl phenol, and 2-cyclohexyl-6-methyl phenol. In this regard, it should be emphasized that 2,6-dialkylphenols wherein both alkyl substituents are tertiary alkyl groups may not be employed in accordance with the present invention. This is contrary to many of the teachings in the art which indicate that 2,6-ditertiaryalkylphenols such as 2,6-ditertiarybutylphenol and the most easily oxidatively coupled of the phenols.

Representative 2,3,6-trialkylphenols which may be utilized in accordance with the present invention include, for example, 2,3,6-trimethyl phenol, 2,3,6-triethyl phenol, 2,6-dimethyl-3-ethyl phenol, 2,3-diethyl-6-tertiary-butyl phenol, 2,3,6-tridecyl phenol, and 2-octyl-3-decyl-6-dodecyl phenol.

Representative 2,3,5,6-tetraalkylphenols which may be utilized in accordance with the present invention include, for example, 2,3,5,6-tetramethyl phenol, 2,3,5-trimethyl-6-tertiarybutyl phenol, 2,3,6-trimethyl-5-tertiary-butyl phenol, 2,3-dimethyl-5,6-diethyl phenol, 2,3,5,6-tetradodecyl phenol, and 2-methyl-3-ethyl-5-isopropyl-6-butylphenol.

When an ortho, para substituted alkylphenol is employed the coupling reaction proceeds in accordance with the following reaction resulting in the o,o' coupled product.

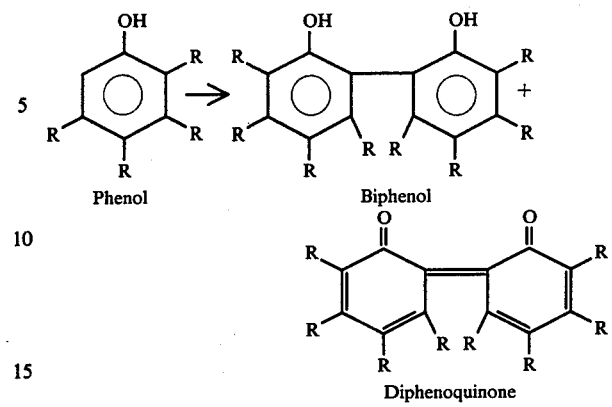

In this reaction R represents hydrogen or an alkyl group as defined above depending upon whether a di, tri, or tetra substituted alkylphenol is utilized.

Similarly, with the ortho, ortho substituted alkylphenols, the reaction results in the p, p' coupled product in accordance with the following reaction wherein R is hydrogen or alkyl depending upon which of the above-mentioned alkylphenols is used as the starting material.

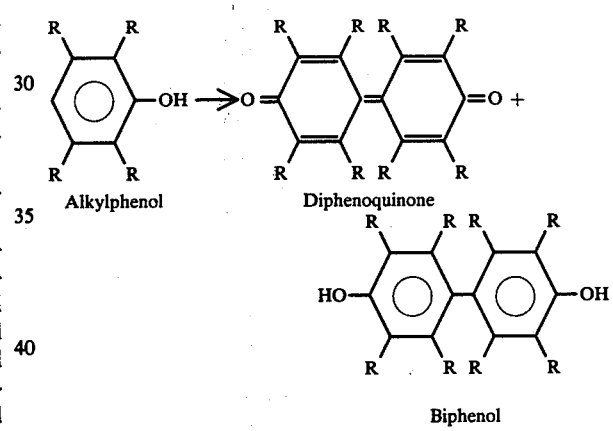

It has also been found that certain alkoxyphenols may be employed in the process of the present invention. These include 2,6 disubstituted phenols wherein at least one of the substituents is an alkoxy group containing up to about six carbon atoms such as methoxy, ethoxy, propoxy, butoxy and pentoxy. In addition to the 2,6 dialkoxyphenols, 2-alkyl-6-alkoxyphenols, wherein the alkyl groups are as defined above for the alkylphenols, may be utilized. As used herein the term alkoxyphenols is intended to include both types of compounds. These compounds may be represented by the following general formulas:

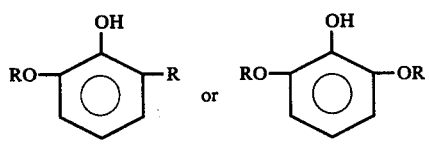

wherein R is an alkyl group containing from 1 to about 12 carbon atoms and OR is an alkoxy group consisting from 1 to about 6 carbon atoms. As above, R may be either methyl or a primary, secondary or tertiary alkyl and may contain from 1 to about 12 carbon atoms and preferably contains from 1 to about 5 carbon atoms. Representative alkoxyphenols which may be utilized include, for example, 2,6-dimethoxyphenol, 2,6-diethoxyphenol, 2,6-dibutoxyphenol, 2-methoxy,6-pentoxyphenol, 2-methyl-6-methoxyphenol, 2-decyl-6-butoxyphenyl and 2-ethyl-6-propoxyphenol.

When these phenols are utilized the reaction proceeds in accordance with the following representative reaction resulting in the p, p' coupled material.

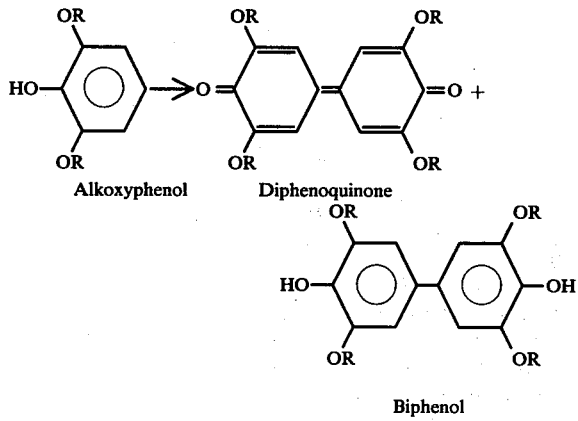

Mixtures of 2 different phenols may also be utilized. When this is done, there generally results a mixture of three different materials. Two of these are the products of the oxidative coupling of one mol of one of the phenols with a second mol of the same phenol. The third product is that resulting from the oxidative coupling of one mol of the first phenol with one mol of the second phenol. The products may be separated prior to use.

Finally, 1-naphthol and substituted 1-naphthols having at least 1 unsubstituted position ortho or para to the hydroxyl group may be employed. The preferred naphthols which may be coupled in accordance with the present invention are represented by the following general formula:

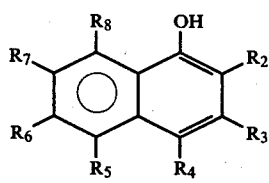

wherein $R_2$, $R_3$ and $R_4$ are hydrogen, alkyl containing from 1 to 5 carbon atoms, or alkoxy containing from 1 to 6 carbon atoms, provided that either $R_2$ or $R_4$ must be hydrogen and, preferably, both $R_2$ and $R_4$ are hydrogen; and $R_5$, $R_6$, $R_7$ and $R_8$ are hydrogen, alkyl containing from 1 to 5 carbon atoms or alkoxy containing from 1 to 6 carbon atoms provided that tertiary alkyl or alkoxy groups may not be attached to adjacent carbon atoms of the naphthalene molecule.

Representative naphthols which may be utilized include, for example, 1-naphthol, 2-methyl-1-naphthol, 2,3-dimethyl-1-naphthol, 4-ethyl-1-naphthol, and 2-methoxy-1-naphthol.

When a naphthol is employed, the coupling reaction takes place in accordance with the following general reactions depending upon the reactive positions — i.e., those either ortho or para to the hydroxy group — available. Thus, if $R_2$ is hydrogen and $R_4$ is alkyl or alkoxy

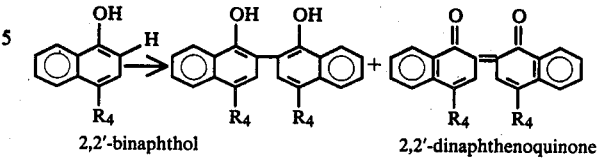

Similarly, if $R_4$ is hydrogen and $R_2$ is alkyl or alkoxy, the products are the 4,4'-binaphthols and the 4,4'-dinaphthenoquinone. When both $R_2$ and $R_4$ are hydrogen the products may be a mixture of the 2,2'-4,4'-binaphthols and dinaphthenoquinones.

Metal Complex

As mentioned above, in accordance with the present invention, the catalyst system comprises, as an essential component thereof, a metal complex of an amino acid. Representative acids which may be used in said complexes include both amino carboxylic acids, i.e., those conventionally referred to simply as amino acids, and amino sulfonic acids. Both of these are sometimes referred to hereinafter simply as amino acids.

In accordance with the present invention it has been found that both primary amino acids, i.e., those containing an $NH_2$ group, secondary amino acids, i.e., those containing an NHR group and tertiary amino acids. i.e., those containing an -NRR group may be employed in the catalyst system of the present invention. Representative amino acids which may be utilized include those selected from the following group: alpha-aminocarboxylic acids, alpha-aminosulfonic acids, mono-N-substituted alpha aminocarboxylic acids, N,N-dialkyl aminocarboxylic acids, mono-N-substituted alpha aminosulfonic acids, N,N-dialkyl aminosulfonic acids, mono-ortho amino aromatic acids, and beta amino carboxylic acids.

Alpha aminocarboxylic acids, i.e., those in which the carboxyl and amino groups are attached to the same carbon atom, may be represented by the following general formula:

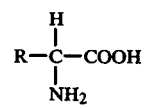

Representative alpha aminocarboxylic acids which may be employed include aliphatic, aromatic, and hydroxyamino acids. Specific compounds which may be utilized include, for example, those given in the following list wherein R in the above formula is as identified in said list.

| NAME | R |
|---|---|
| Glycine | H— |
| Alanine | $CH_3$— |
| α-Aminobutyric acid | $CH_3-CH_2$— |
| Novaline | $CH_3-CH_2-CH_2$— |
| Valine | $CH_3$<br>    \<br>     CH—<br>    /<br>$CH_3$ |
| Norleucine | $CH_3-CH_2-CH_2-CH_2$— |

| NAME | R |
|---|---|
| Isoleucine | CH₃\CH—<br>C₂H₅/ |
| Serine | HO—CH₂— |
| Leucine | CH₃\  H<br>   \C—CH₂—<br>CH₃/ |
| Homoserine | HO—CH₂—CH₂— |
| Aspartic Acid | HOOC—CH₂— |
| Glutamic Acid | HOOC—CH₂—CH₂— |
| Phenylalanine | ⌬—CH₂— |
| Tyrosine | HO—⌬—CH₂— |
| Dihydroxyphenylalanine | OH<br>HO—⌬—CH₂— |
| 3-iodotyrosine | I<br>HO—⌬—CH₂— |
| 3,5-diiodotyrosine | I<br>HO—⌬—CH₂—<br>I |
| 3,5-dibromotyrosine | Br<br>HO—⌬—CH₂—<br>Br |
| 3,5,3'triiodothyronine | I     I<br>HO—⌬—O—⌬—CH₂—<br>I |
| Thyroxine | I     I<br>HO—⌬—O—⌬—CH₂—<br>I     I |
| Ornithine | H₂N—CH₂—CH₂—CH₂— |
| Lysine | H₂N—CH₂—CH₂—CH₂—CH₂— |
| Hydroxylysine | OH<br>H₂N—CH₂—CH—CH₂—CH₂— |
| Cysteine | HS—CH₂— |
| Homocysteine | HS—CH₂—CH₂— |
| Methionine | CH₃—S—CH₂—CH₂— |
| Cystine | NH₂<br>HOOC—CH—CH₂—S—S—CH₂— |
| P-hydroxy phenyl glycine | HO—⌬— |
| Asparagine | H₂NOC—CH₂— |
| Glutamine | H₂NOC—CH₂—CH₂— |
| Phosphoserine | H₂O₃PO—CH₂— |
| Histidine | [imidazole]—CH₂— |
| Tryptophan | [indole]—C=CH<br>          |<br>          CH |

| NAME | R |
|---|---|
| Arginine | NH<br>HN=C—N—CH₂—CH₂—CH₂—<br>       H |
| Citrulline | NH₂<br>O=C<br>   \NH—CH₂—CH₂—CH₂— |

Alpha aminosulfonic acids — i.e., those in which both the sulfonyl and amino groups are attached to the same carbon atom — may be represented by the following general formula:

$$R-\underset{\underset{NH_2}{|}}{\overset{\overset{H}{|}}{C}}-SO_3H$$

Representative alpha aminosulfonic acids, wherein R is hydrogen or an alkyl group which may be employed are given in the following list:

| NAME | R |
|---|---|
| amino-methane sulfonic acid | H |
| amino-ethane sulfonic acid | CH₃— |
| amino-hexane sulfonic acid | CH₃CH₂CH₂CH₂— |

Ortho amino aromatic acids include benzene and naphthalene derivatives wherein the amino and acid substituent are on adjacent carbon atoms. These materials are represented by the following general formulas:

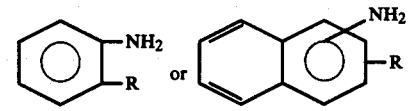

wherein R is either -COOH or -SO₃H. Representative compounds which may be utilized include the following:
  o - amino benzoic acid,
  o - amino benzene sulfonic acid,
  1-amino-2-naphthoic acid,
  2-amino-3-naphthioc acid,
  1-amino-2-naphthalene sulfonic acid,
  2-amino-1-naphthalene sulfonic acid, and
  2-amino-3-naphthalene sulfonic acid.

N-substituted alpha aminocarboxylic acids may also be employed in the present invention. These compounds are represented by the following general formulas:

$$R-\underset{\underset{NHR'}{|}}{\overset{\overset{H}{|}}{C}}-COOH \qquad (a)$$

$$R''-\underset{\underset{NH}{|}\diagdown}{\overset{\overset{H}{|}}{C}}-COOH \qquad (b)$$

Representative materials having formula (a) above include alkyl, acyl and aryl substituted compounds — i.e., those in which R' is one of said groups. Examples of these compounds are given in the following list:

| NAME | R | R' |
|---|---|---|
| N-acetylglycine | H | CH₃CO— |
| N-methylglycine | H | CH₃— |
| N-phenylglycine | H | —C₆H₅ |
| glycylglycine | H | H₂N—CH₂—CO— |
| glutathione | H | HOOC—CH(NH₂)—CH₂CH₂—C(O)—N(H)—CH(CH₂SH)—C(O)— |

Examples of compounds coming within formula (b) above include the following, wherein R″ is a hydrocarbon or substituted hydrocarbon radical containing sufficient carbon atoms to result in a compound containing a stable ring structure — i.e., generally about 3 carbon atoms.

| NAME | R″ |
|---|---|
| proline | —CH₂—CH₂—CH₂— |
| hydroxyproline | —CH₂—CH(OH)—CH₂— |
| pyrrolidone carboxylic acid | —C(O)—CH₂—CH₂— |

N,N dialkyl alpha aminocarboxylic acids wherein the alkyl groups contain from 1 to about 12 carbon atoms and preferably from 1 to about 5 carbon atoms may be utilized. Representative compounds include, for example, N,N dimethylglycine, N-methyl-N-ethylglycine and N,N didodecylglycine.

N-substituted alpha aminosulfonic acids having one of the following general formulas wherein R' and R″ are as defined above for the N-substituted alpha aminocarboxylic acids and R is hydrogen or an alkyl group may also be employed.

N,N dialkyl alpha aminosulfonic acids wherein the alkyl groups contain from 1 to about 12 carbon atoms and preferably from 1 to about 5 carbon atoms may also be employed. Representative compounds include those having the following general formula

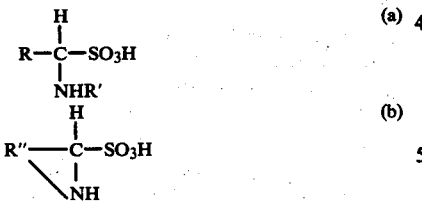

wherein R' is an alkyl group.

Finally, beta aminocarboxylic acids — i.e., those in which the carboxyl and amino groups are attached to adjacent carbon atoms, may also be utilized. These acids are represented by the following general formula:

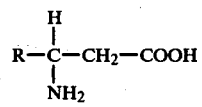

Representative beta amino acids wherein R is hydrogen, alkyl or aryl which may be utilized include the following:

| NAME | R |
|---|---|
| Beta Alanine | H |
| Beta amino butyric acid | CH₃ |
| Beta amino phenyl propionic acid | —C₆H₅ |

Prior to use in the present invention, the amino acids are converted to a metal complex thereof. As used herein the term metal complex refers to the product obtained by reacting a source of the desired metal ion with an aminocarboxylic or an aminosulfonic acid. With the divalent metal ions employed in preparing the complexes used in carrying out the present invention, it is preferred that equivalent amounts of metal ion and acid be reacted — i.e., about two mols of acid per mol of metal ion. In accordance with the present invention it has been found to be critical to the preparation of carbon-carbon coupled products that either a cupric, cobaltous, manganous or nickelous complex of the acid be employed.

These complexes may be prepared in any manner and the preparation thereof has not been found to be critical to the present invention. The following three methods have generally been employed but other methods which will be readily apparent to those skilled in the art from the description of the invention given herein, may also be utilized.

First, equivalent amounts of the aminocarboxylic or aminosulfonic acid and a source of cupric, cobaltous, manganous or nickelous ions may be combined in a suitable medium such as water and reacted to form the complex. If a copper, cobalt, manganese or nickel salt is employed, such as cupric acetate, an amount of a basic compound sufficient to neutralize the acid generated during the course of the complex forming reaction should be added. Similarly, if the amino acid used is in the form of an amine unit such as the hydrochloride, an amount of a basic compound sufficient to neutralize the acidic portion should be utilized. As used in this section, a basic compound is any material an aqueous solution of which has a pH above 7. Although not essential, it is preferred to employ as said basic compound one of the alkaline materials described below. The complex is prepared by simply stirring the solution for a period of time. If desired, heat may be applied to accelerate formation of the complex.

Alternatively, the amino acid and the source of the metal ion may simply be combined and added to the reaction mixture wherein the complex of the amino acid is formed. When this is done any basic compound required to neutralize any acidic by-products of the complex forming reaction is also added directly to the reaction mixture.

Finally, the amino acid, source of metal ion, and any required basic compound may be added separately to the reaction medium and the complex formed in situ. As mentioned above, the method by which the metal complex is prepared has not been found to be critical to the present invention. However, preferred results have been achieved when the source of metal ion and the amino acid are combined prior to addition to the reaction medium.

The amount of metal complex employed has not been found to be narrowly critical to the process of the present invention. However, it is preferred to employ at least 0.02 mmols of the complex per mol of phenol naphthol. If less than this amount is used, the reaction is slower and the yields are low. Similarly, the maximum amount of complex employed is not generally greater than about 200 mmols of the complex per mol of phenol or naphthol. At amounts much in excess of this the cost of the catalyst may result in an uneconomic system.

Although any of the above-mentioned metal complexes may be used, preferred results have been achieved with the cupric complexes of alpha-aminocarboxylic acids. Especially preferred results are achieved when cupric glycinate is employed as the metal complex.

As mentioned above, an advantage of the catalyst system and of the process of the present invention is that the reaction can be carried out in an aqueous medium instead of an organic solvent as has been used in prior art systems. However, it has not been found to be critical to the present invention to employ a water soluble metal complex. Thus, materials which are insoluble in water as well as those which are soluble may be utilized.

Although not essential to the present invention, an alkaline material as defined below may also be included in the reaction mixture. Preferred results have been achieved when such a material is employed.

Alkaline Material

In accordance with the present invention, there may also be included in the catalyst system an alkaline material. It has been found that the use of an alkaline material in the present system increases the conversion to carbon-carbon coupled products and decreases the conversion to carbon-oxygen coupled products. The use of such a material also increases the rate of the oxidative coupling reaction, increases the total yield of product, and decreases the amount of the metal complex which must be utilized.

The alkaline material useful in achieving these improved results is selected from the group consisting of alkali metal hydroxides, alkali metal carbonates, and alkali metal bicarbonates. The alkaline material may be added either as a single compound or as a mixture of compounds. Representative materials which may be employed include, for example, sodium hydroxide, potassium hydroxide, lithium hydroxide, sodium carbonate, lithium carbonate, sodium bicarbonate, rubidium carbonate, rubidium hydroxide, cesium bicarbonate, and cesium hydroxide.

The amount of alkaline material employed has not been found to be narrowly critical. However, preferred results are achieved when the amount of said material is equal to at least about 6 mmols per mol of phenol or naphthol. At this amount it has been found that the rate of the reaction is acceptable for most operations. Similarly, except in the case of the 2,4,6 tri-substituted phenols which are discussed in detail below, the maximum amount of alkaline material is preferably not greater than about 100 mmols per mol of phenol or naphthol. In this regard it should be noted that it is preferred to maintain the pH of the reaction mixture at from about 6 to about 10 during the course of the reaction and it is again emphasized that additional alkaline material may be required to neutralize any acidic components introduced into the reaction mixture during the formation of the metal complex. The amount of material employed for this purpose should be sufficient to neutralize said acid and is in addition to the amount of alkaline material mentioned above in this section.

Besides the selective production of carbon-carbon coupled products, an additional advantage of the catalyst system of the present invention is the ability to control the type of carbon/carbon coupled product produced. Thus, it is possible to prepare selectively either diphenoquinone or biphenol or dinaphthenoquinone or binaphthol in accordance with the present invention. This result is achieved by controlling the amount of alkaline material and/or metal complex included in the system. Generally, as the amount of alkaline material or metal complex is increased, the percentage of diphenoquinone or dinaphthenequinone in the resulting product also increases. Also, it has been found that as the reaction temperature or oxygen pressure is increased the percentage of quinone-type product decreases.

As mentioned above, an advantage of the process of the present invention is that it makes it possible for the oxidably coupling reaction to be carried out in an aqueous medium. The amount of water employed has not been found to be critical to the present invention and any amount of water which will permit the reaction mixture to be stirred during the course of the reaction may be employed. It should also be noted again that it is not essential that the various components be soluble in water and the term aqueous mixture as used herein is intended to include solutions, slurries, suspensions and the like.

The components of the reaction mixture may be combined in any suitable manner. Thus, the phenol or naphthol, metal complex, alkaline material, if any, and water may be combined in any order in a suitable reaction vessel. In a preferred method, the phenol or naphthol and metal complex are combined in water in a suitable reaction vessel, the mixture is heated to from 50° C. to 60° C. and an aqueous solution of the alkaline material is added. In modifications of this procedure the alkaline material may be added prior to heating or the metal complex and alkaline material may be combined prior to addition to the reaction mixture.

The reaction mixture comprising phenol or naphthol, water, metal complex, and alkaline material, if any, is contacted with a suitable oxidizing agent to convert the phenol or naphthol to the desired product. Oxidizing agents which may be employed in carrying out the present invention include oxygen either alone or as an oxygen-containing gas, such as air. The oxygen may be introduced into the reaction mixture either directly as oxygen gas or as an oxygen-generating material such as oxone, hydrogen peroxide, or an organic peroxide. The amount of oxygen utilized should be sufficient to convert all of the phenol or naphthol to the desired product and, to assure that sufficient oxygen is present, oxygen should be introduced into the reaction mixture continuously during the course of the reaction.

Although not essential to the process of the present invention, especially preferred results are achieved when there is also included in the reaction mixture a surfactant. A variety of surfactants are well known in the art and, as used herein, the term surfactant is intended to refer to organic compounds that contain in the molecule two dissimilar structural groups, such as a water-soluble and water-insoluble moiety.

Surfactants are often classified, based on the hydrophilic (water liking) group which they contain, as either anionic, cationic, nonionic, or amphoteric. Any of these types of surfactants may be utilized. In selecting a surfactant, the only criteria are (a) that it be inert—i.e., one which will not oxidize or otherwise interfere with the oxidative coupling reaction and (b) that it be capable of keeping the heterogeneous phases of the reaction mixture suspended. Although it does not affect the total yield or quality of the product, the surfactant facilitates stirring and removal of the product from the reaction vessel when the process has been completed. A variety of surfactants which may be employed are described, for example, in Kirk-Othmer, *Encyclopedia of Chemical Technology*, 2nd Edition, Volume 19, Interscience Publishers, New York, 1969 at pages 507–593. Representative surfactants which may be employed include, for example, sodium lauryl sulfate, sodium dodecyl benzene sulfonate, sodium di(2-ethylhexyl)phosphate, polyoxyethylene nonylphenol, polyoxyethylene octylphenol, polyoxyethylene oleyl, alcohol, polyoxyethylene tridecyl alcohol, glycerol monooleate, glycerol dieleate, glycerol monostearate, sorbitan monolaurate, sorbitan tristearate, polyoxyethylene sorbitan monooleate, ethylene glycol stearate, diethylene glycol oleate, polyethyleneglycol monolaurate, polyoxyethylene stearylamine, polyoxyethylene tallowamine, 2-heptadecyl-1-(hydroxyethyl)-2-imidazoline, distearyldimethylammonium chloride, cetylbenzyldimethylammonium chloride, lauryltrimethylammonium bromide, cetylpyridinium chloride, N-coco-3 amino-propionic acid, (1-carboxyheptadecyl) trimethylamminium hydroxide and 1,1-bis (carboxymethyl)-2-undecyl-2-imidazolinium hydroxide, disodium salt.

The reaction conditions—i.e., time and temperature—employed have not been found to be narrowly critical to the process of the present invention. Preferred results have been achieved when the reaction mixture is maintained at from about 80° C. to 90° C. during the course of the reaction. However, temperatures above and below this preferred range may be utilized. At lower temperatures the reaction rate is reduced and at temperatures below about 40° C. is so slow as to result in an uneconomic system. Similarly, when operating at atmospheric pressure, as is desirable in some commercial operations, the practical upper limit on the temperature is 100° C., the boiling point of the water.

The amount of time required for completion of the reaction depends on the temperature employed and the other variables such as the concentration of phenol or naphthol and the amount of metal complex and alkaline material employed. However, it has been found that, in general, the reaction is completed in 6 hours or less. If the reaction is conducted at elevated oxygen pressure, the time required will be less.

Although, as mentioned above, the process of the present invention results primarily in the production of carbon-carbon coupled products, there are also sometimes included in the solids removed from the reaction mixture the following: (a) unreacted phenol or naphthol, and (b) low molecular weight polyphenoxy ether. The polyphenoxy ether and phenol or naphthol may be removed by washing the solids with a solvent in which these materials are soluble, such as an aromatic hydrocarbon—e.g., benzene or a halogenated solvent—e.g., methylene chloride. If it is desired to separate the materials from each other and from the solvent, this may be done by distillation.

If the reaction results in the mixture of biphenol and diphenoquinone or binaphthol and dinaphthenoquinone, these materials may be separated by any method known in the art. An especially convenient way of separating the materials is to stir the solid product with a dilute aqueous solution of sodium hydroxide, which has the effect of converting the biphenol or binaphthol to the sodium salt which is soluble in water. The insoluble diphenoquinone or dinaphthenoquinone may then be filtered off and the biphenol or binaphthol recovered by adding the aqueous solution of the sodium salt thereof to a dilute solution of an acid such as hydrochloric or acetic from which the biphenol or binaphthol precipitates. Alternatively, the entire product may be hydrogenated or chemically reduced and converted to the biphenol or binaphthol.

When the metal-amino acid complex is insoluble in water, it has been found that during the course of the reaction the material is in some way changed so that it dissolves in the reaction medium. Thus, it has not been found to be necessary to employ any special techniques to remove this material from the reaction medium at the termination of the process. However, it is desirable to remove any residual metal remaining in the products. This may be accomplished by filtering off the desired product, washing the solids with a dilute solution of a strong acid such as hydrochloric acid to remove the metal, followed by a water wash to remove the hydrochloric acid.

The diphenoquinones and/or biphenols as well as the binaphthols and dinaphthenoquinones produced in accordance with the present invention are suitable for any of the uses of these types of materials which uses have heretofore been described in the art. Thus, the diphenoquinones and dinaphthenoquinones may be used as inhibitors of oxidation, peroxidation, polymerization and gum formation in gasolines, aldehydes, fatty oils, lubricating oils, ethers and similar compounds. As mentioned in U.S. Pat. No. 2,905,674 issued to Filbey, the diphenoquinones may also be hydrogenated, employing conventional techniques, to yield the corresponding biphenols. The biphenols may be employed as stabilizers in gasoline and other petroleum products as described in U.S. Pat. No. 2,479,948 issued to Luten et al.

The catalyst system of this invention may also be employed to prepare coupled products of alkylphenols wherein all of the positions ortho and para to the hydroxy group are substituted and the substituent para to the hydroxy group is methyl. These alkylphenols may be represented by the following general formula:

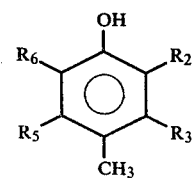

wherein

R$_3$ and R$_5$ are hydrogen, alkyl groups containing from 1 about 5 carbon atoms or alkoxy groups containing from 1 to about carbon atoms, provided that if both R$_3$ and R$_5$ are alkyl or alkoxy groups only one of these groups may be a tertiary alkyl or alkoxy and R$_2$ and R$_6$ are a primary, secondary or tertiary alkyl containing from 1 to about 12 carbon atoms or an alkoxy group containing from 1 to about 12 carbon atoms provided that only one of said substituents may be a tertiary alkyl or alkoxy.

Representative compounds which may be employed include, for example, 2,4,6-trimethyl phenol; 2,6-di-secondary butyl-4-methyl phenol; 2-methyl-6-t-butyl-4-methyl phenol; and 2,3,4,6-tetramethyl phenol.

When one of these alkylphenols is employed the reaction proceeds in accordance with the following general reaction to produce the stilbenequinone or bisphenol derivative. These materials are useful in the same applications set forth above for the diphenoquinones, dinaphthenoquinones, biphenols and binaphthols

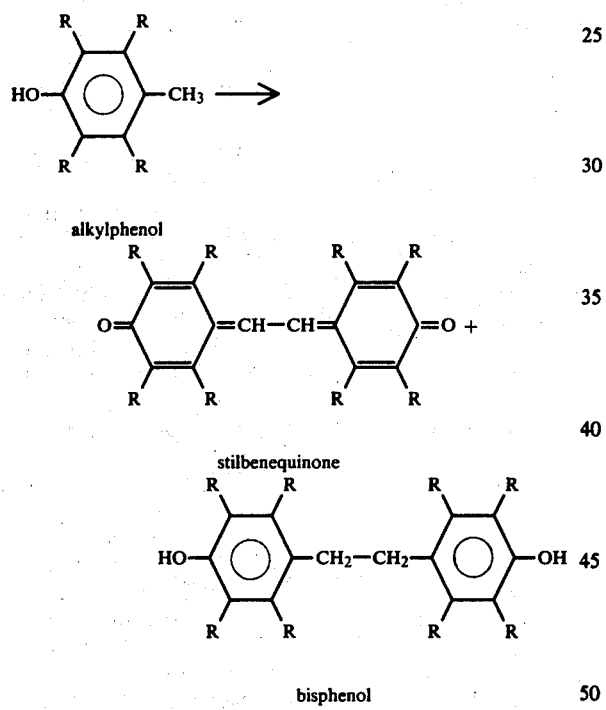

In carrying out this reaction, the same procedures and conditions are employed as those given above for the other alkylphenols, alkoxyphenols and naphthols. However, with these particular phenols it has been found that the preferred amount of alkaline materials employed is equal to at least about 1 mol per mol of phenol. When less than this amount is utilized the total conversion as well as the yield of carbon-carbon coupled product are reduced.

In order to describe the present invention so that it may be more clearly understood, the following examples are set forth. These examples are set forth primarily for the purpose of illustration and any enumeration of detail contained therein should not be interpreted as a limitation on the concept of the present invention.

As used herein, the term mol percent refers to:

$$\frac{\text{mols of product (actual)}}{\text{mols of product (theoretical)}} \times 100$$

Ultrawet K, soft refers to sodium dodecylbenzene sulfonate.

EXAMPLE 1

Into a first flask there were added:
0.40 grams (2 mmols) of cupric acetate monohydrate,
0.30 grams (4 mmols) of glycine, and
50 ml of ion exchanged water.

Into a 500 ml creased Morton flask, fitted with a gas addition tube, a condenser, a thermometer, and a stirrer capable of operating at speeds in the range of from about 8,000 to about 10,000 rpm, there were added:
48.8 grams (400 mmols) of 2,6-xylenol, and
150 ml of ion exchanged water.

To the resulting slurry there was added the copper/glycine composition prepared above. The resulting mixture was stirred under oxygen and heated to a temperature of 50° C. There was then added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the solids washed with water. A sample of the solid was removed, dissolved in acetone and analyzed by gas-liquid chromatography. The analysis indicated that 1 mol percent of the 2,6-xylenol was unreacted.

The dried solid weighing 43.8 grams was washed twice with 100 ml of benzene to remove 2,6-xylenol and polyphenoxy ether. The resulting solid was dried at 60° C. Analysis of the product indicated a yield of tetramethyl diphenoquinone equal to 44.2 mol percent. The yield of tetramethylbiphenol was calculated as 34.7 mol percent.

EXAMPLE 2

Into a first flask there were added:
0.40 grams (2 mmols) of cupric acetate monohydrate,
0.41 grams (4 mmols) of 2-aminobutyric acid, and
25 ml of ion exchanged water.

To the resulting clear, dark blue mixture there was added 4.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
48.8 grams (400 mmols) of 2,6-xylenol,
0.2 grams of Ultrawet K soft (sodium dodecyl benzene sulfonate), and
200 ml of ion exchanged water.

To the resulting solution there was added 100 ml of the composition prepared above. The resulting mixture was stirred under oxygen and heated to a temperature of 50° C. and there was then added 4.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 25° C.

The reaction mixture was filtered, the solid was washed with water, and a sample of the solid was removed, dissolved in acetone and analyzed by gas-liquid chromatography. The analysis indicated that 4 mol percent of the 2,6-xylenol was unreacted.

The solid was air dried and washed twice with 200 ml of benzene to remove 2,6-xylenol and polyphenoxy ether. The resulting black solid was dried at 60° C. Analysis of the product indicated a yield of tetramethylbiphenol equal to 24.4 mol percent and a yield of diphenoquinone equal to 35.0 mol percent.

EXAMPLE 3

Into a first flask there were added:
0.40 grams (2 mmols) of cupric acetate monohydrate,
0.47 grams (4 mmols) of DL-valine, and
50 ml of ion exchanged water.

Into a 500 ml creased Morton flask fitted with a gas addition tube, a condenser, a thermometer, and a stirrer capable of operating at speeds in the range of from about 8,000 to about 10,000 rpm, there were added:
48.8 grams (400 mmols) of 2,6-xylenol,
0.2 grams of Ultrawet K soft, sodium dodecyl benzene sulfonate, and
150 ml of ion exchanged water.

To the resulting solution there was added 100 ml of the catalyst composition prepared above. The resulting mixture was stirred under oxygen and heated to a temperature of 52° C. There was then added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered, and the solids washed with water. A sample of the solid was removed, dissolved in acetone and analyzed by gas-liquid chromatography. The analysis indicated that all of the 2,6-xylenol had reacted.

The solid was air dried and washed twice with 100 ml of benzene to remove 2,6-xylenol and polyphenoxy ether. The resulting dark green solid was dried at 60° C. Analysis of the product indicated a yield of tetramethylbiphenol equal to 39.3 mol percent and a yield of diphenoquinone equal to 45.2 mol percent.

EXAMPLE 4

Preparation of Catalyst Composition

Into a reaction flask there were added:
0.40 grams (2 mmols) of cupric acetate monohydrate,
0.525 grams (4 mmols) of L-Leucine, and
100 ml of ion exchanged water.

To the resulting slurry there was added 4.0 ml of a 1.0 Normal solution of sodium bicarbonate resulting in the formation of a blue solid. The resulting mixture was diluted to 200 ml with water, shaken, and heated to 60° C. When this temperature was reached, the solid still had not dissolved. The mixture was cooled and bottled.

Oxidative Coupling

Into a 500 ml creased, Morton flask fitted with a gas addition tube, condenser, thermometer, and a stirrer capable of operating at speeds in the range of from about 8,000 to about 10,000 rpm there were added:
48.8 grams (400 mmols) of 2,6-xylenol, and 200 ml of the catalyst composition prepared above.

The catalyst composition was rinsed in with 50 ml of water. There was then added 0.2 grams of Ultrawet K, soft. The resulting reaction mixture was stirred under oxygen and heated to a temperature of 50° C. When this temperature was reached, there was added 4.0 ml of a 1.0 Normal sodium bicarbonate solution. The reaction mixture was then heated to a temperature of 80° C. and a slow stream of oxygen was introduced. At the end of 6 hrs., the reaction was flushed with nitrogen and cooled to a temperature of 20° C.

The reaction mixture was filtered, a sample of the solid was removed, dissolved in acetone and analyzed by gas-liquid chromatography. The analysis indicated that 1 mol percent of the 2,6-xylenol was unreacted.

The solid was air dried and washed twice with 100 ml of benzene to remove 2,6-xylenol and polyphenoxy ether. The resulting black solid was dried at 60° C. The diphenoquinone and biphenol were separated by the following procedure.

37.5 grams of the solid were stirred with 1 liter of acetone, filtered, and the solid washed with 100 ml of acetone. The insoluble red diphenoquinone was dried and weighed 16.5 grams. The material melted at 198° C. The acetone filtrate was treated with 1 gram of hydroxylamine hydrochloride and 2 ml of pyridine after which it was poured into 2 volumes of water. The precipitated tetramethylbisphenol was filtered, washed with 200 ml of water and dried at 60° C. The resulting cream-colored solid weighed 21.2 grams and melted at 221° C. The results indicated a yield of tetramethylbiphenol equal to 45.5 mol percent and a yield of diphenoquinone equal to 35.6 mol percent.

EXAMPLE 5

Into a reaction flask there were added:
0.40 grams (2 mmols) of cupric acetate monohydrate,
0.66 grams (4 mmols) of phenylalanine, and
40 ml of ion exchanged water.

To the resulting slurry there was added 4.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
100 ml of ion exchanged water,
48.8 grams (400 mmols) of 2,6-xylenol, and
0.2 grams of Ultrawet K, soft. To the resulting mixture there was added 100 ml of the catalyst composition prepared above.

The catalyst composition was rinsed in with an additional 50 ml of water. The resulting reaction mixture was stirred under oxygen and heated to a temperature of 52° C. When this temperature was reached, there was added 4.0 ml of a 1.0 Normal sodium bicarbonate solution. The reaction mixture was then heated to a temperature of 80° C., and a slow stream of oxygen was introduced. At the end of 6 hrs., the reaction was flushed with nitrogen and cooled to a temperature of 20° C.

The reaction mixture was filtered, a sample of the solid was removed, dissolved in acetone and analyzed by gas-liquid chromatography. The analysis indicated that 25 mol percent of the 2,6-xylenol was unreacted.

The solid was air dried and washed twice with 100 ml of benzene to remove 2,6-xylenol and polyphenoxy ether. The resulting solid was dried at 60° C. Analysis of the product indicated a yield of tetramethylbiphenol equal to 62.5 mol percent.

EXAMPLE 6

Into a 500 ml creased Morton flask, fitted with a gas addition tube, a condenser, thermometer, and a stirrer capable of operating at speeds in the range of from about 8,000 to about 10,000 rpm, there were added:
  48.8 grams (400 mmols) of 2,6-xylenol,
  250 ml of ion exchanged water,
  4.0 ml of a 1.0 Normal solution of sodium bicarbonate, and
  0.2 grams of Ultrawet K, soft.

The resulting mixture was heated to 50° C. and there was then added 0.25 grams of cupric glutamate.

The reaction mixture was then heated to a temperature of 80° C. and a slow stream of oxygen was introduced. At the end of 6 hrs., the reaction was flushed with nitrogen and cooled to a temperature of 20° C.

The reaction mixture was filtered. A sample of the solid was removed, dissolved in acetone and analyzed by gas-liquid chromatography. The analysis indicated that 12 mol percent of the 2,6-xylenol was unreacted.

The solid was washed with water, dried and washed twice with 50 ml of benzene to remove 2,6-xylenol and polyphenoxy ether. The resulting solid was dried at 60° C. Analysis of the product indicated a yield of tetramethylbiphenol equal to 56.5 mol percent.

The cupric glutamate was prepared in accordance with the following procedure:

Into a suitable reaction flask there were added:
  7.36 grams (0.05 mol) of glutamic acid, and 200 ml of water.

There was then added approximately 50 ml of dilute sodium hydroxide solution until the pH of the mixture was equal to 7.5 and all of the glutamic acid had dissolved. At this time there was added 4.99 grams (0.025 mols) of cupric acetate. The pH decreased to 4.6 and the solution turned a deep blue color. The pH was adjusted to 8.0 with dilute sodium hydroxide. The reaction mixture was stripped under vacuum and the residue treated with a mixture of ethanol and water. The insoluble fraction was filtered and dried at 80° C. There resulted 5.0 grams of cupric glutamate.

EXAMPLE 7

Into a first reaction flask thre were added:
  0.40 grams (2 mmols) of cupric acetate monohydrate,
  0.34 grams (4 mmols) of L(+)ornithine hydrochloride, and
  50 ml of ion exchanged water.

To the resulting clear, dark blue solution there was added 8.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
  48.8 grams (400 mmols) of 2,6-xylenol,
  0.2 grams of Ultrawet K soft, and
  200 ml of ion exchanged water.

To the resulting solution there was added the catalyst composition prepared above. The resulting mixture was stirred under oxygen and heated to a temperature of 50° C. There was then added 4.0 ml of a 1.0 Normal sodium bicarbonate solution.

The reaction mixture was heated at a temperature of 80° C. and a slow stream of oxygen was introduced. At the end of 6 hrs., the reaction was flushed with nitrogen and cooled to a temperature of 20° C.

The reaction mixture was stirred with acetone, filtered and the solids were washed with 200 ml of benzene to remove 2,6-xylenol and polyphenoxy ether. The resulting solid was dried at 60° C. Analysis of the product indicated a yield of tetramethylbiphenol equal to 50 mol percent.

EXAMPLE 8

Into a reaction flask there were added:
  0.40 grams (2 mmols) of cupric acetate monohydrate,
  0.72 grams (4 mmols) of lysine hydrochloride, and
  50 ml of ion exchanged water.

To the resulting clear, dark blue solution there was added 8.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
  48.8 grams (400 mmols) of 2,6-xylenol,
  0.2 grams of Ultrawet K soft, and
  200 ml of ion exchanged water.

To the resulting solution there was added 50 ml of the catalyst composition prepared above. The resulting mixture was stirred under oxygen and heated to a temperature of 50° C. There was then added 4.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled.

The solids were separated from the reaction mixture, dried, and washed twice with 50 ml of benzene to remove 2,6-xylenol and polyphenoxy ether. The resulting solid was dried, slurried in water and treated with solid sodium hydroxide until a red slurry resulted. The solid diphenoquinone was filtered and dried at 60° C. The yield was equal to 31 mol percent. The filtrate was poured into dilute hydrochloric acid from which the biphenol precipitated. The solid biphenol was filtered, washed with water and dried at 60° C. The yield of biphenol was equal to 18.7 mol percent.

EXAMPLE 9

Into a reaction flask there were added:
  0.40 grams (2 mmols) of cupric acetate monohydrate,
  0.60 grams (4 mmols) of methionine, and
  25 ml of ion exchanged water.

To the resulting clear, slurry there was added 4.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
  48.8 grams (400 mmols) of 2,6-xylenol,
  0.2 grams of Ultrawet K soft, and
  150 ml of ion exchanged water.

To the resulting solution there was added 50 ml of the catalyst composition prepared above. The resulting mixture was stirred under oxygen and heated to a temperature of 50° C. There was then added 4.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered. The solid was air dried and washed twice with 100 ml of benzene to remove 2,6-xylenol and polyphenoxy ether. The resulting solid was dried at 60° C. Analysis of the product indicated a yield of tetramethylbiphenol equal to 73 mol percent.

EXAMPLE 10

Into a reaction flask there were added:
0.40 grams (2 mmols) of cupric acetate monohydrate,
0.84 grams (4 mmols) of L(+)histidine hydrochloride, and
100 ml of ion exchanged water.

To the resulting clear, dark blue solution there was added 8.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
48.8 grams (400 mmols) of 2,6-xylenol,
0.2 grams of Ultrawet K soft, sodium dodecyl benzene sulfonate, and
150 ml of ion exchanged water.

To the resulting solution there was added 100 ml of the catalyst composition prepared above. The resulting mixture was stirred under oxygen and heated to a temperature of 60° C. When the temperature reached 60° C. there was added 4.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 25° C.

The reaction mixture was filtered, a sample of the solid was air dried and washed twice with 100 ml of benzene to remove 2,6-xylenol and polyphenoxy ether. The resulting brown solid was dried at 60° C. Analysis of the product indicated a yield of tetramethylbiphenol equal to 54 mol percent.

EXAMPLE 11

Into a reaction flask there were added:
0.40 grams (2 mmols) of cupric acetate monohydrate,
0.55 grams (4 mmols) of anthranilic acid, and
50 ml of ion exchanged water.

Into a 500 ml creased Morton flask fitted with a gas addition tube, a condenser, a thermometer, and a stirrer capable of operating at speeds in the range of from about 8,000 to about 10,000 rpm, there were added:
48.8 grams (400 mmols) of 2,6-xylenol,
0.2 grams of Ultrawet K soft, sodium dodecyl benzene sulfonate, and
200 ml of ion exchanged water.

To the resulting solution there was added the catalyst composition prepared above. The resulting mixture was stirred under oxygen and heated to a temperature of 55° C. at which time there was added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 25° C.

The reaction mixture was filtered, the solid was washed with water and air dried. The dry solid was washed twice with 200 ml of benzene to remove 2,6-xylenol and polyphenoxy ether and air dried at 60° C. Analysis of the product indicated a yield of tetramethylbiphenol equal to 54.8 percent.

EXAMPLE 12

Into a reaction flask there were added:
0.40 grams (2 mmols) of cupric acetate monohydrate,
0.44 grams (4 mmols) of amino methane sulfonic acid, and
40 ml of ion exchanged water.

To the resulting solution there was added 4.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
190 ml of ion exchanged water,
48.8 grams (400 mmols) of 2,6-xylenol, and
0.2 grams of Ultrawet K soft.

To the resulting mixture there was added 60 ml of the catalyst composition prepared above.

The resulting reaction mixture was stirred under oxygen and heated to a temperature of 55° C. When this temperature was reached, there was added 4.0 ml of a 1.0 Normal sodium bicarbonate, solution. The reaction mixture was then heated to a temperature of 80° C. and a slow stream of oxygen was introduced. At the end of 6 hrs., the reaction was flushed with nitrogen and cooled to a temperature of 20° C.

The reaction mixture was filtered, a sample of the solid was removed, dissolved in acetone and analyzed by gas-liquid chromatography. The analysis indicated that 20 mol percent of the 2,6-xylenol was unreacted.

The water-washed solid was air dried and washed twice with 100 ml of benzene to remove 2,6-xylenol and polyphenoxy ether. The resulting solid was dried at 60° C. Analysis of the product indicated a yield of tetramethylbiphenol equal to 31.4 mol percent.

EXAMPLE 13

Into a reaction flash there were added:
0.40 grams (2 mmols) of cupric acetate monohydrate,
0.73 grams (4 mmols) of aniline-2-sulfonic acid, and
50 ml of ion exchanged water.

To the resulting solution there was added 4.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
48.8 grams (400 mmols) of 2,6-xylenol,
0.2 grams of Ultrawet K soft, and
200 ml of ion exchanged water.

To the resulting solution there was added 50 ml of the catalyst composition prepared above. The resulting mixture was stirred under oxygen and heated to a temperature of 53° C. When the temperature reached 53° C. there was added 4.0 ml of a 1.0 Normal sodium bicarbonate solution.

The reaction mixture was heated to a temperature of 80° C. and a slow stream of oxygen was introduced. At the end of 6 hrs. the reaction was flushed with nitrogen and cooled to a temperature of 20° C.

The reaction mixture was evaporated. The solids were stirred into 200 ml of benzene to remove 2,6-xylenol and polyphenoxy ether. The resulting solids were filtered, washed with benzene, washed with water, and dried at 60° C. Analysis of the product indicated a yield of tetramethylbiphenol equal to 41 mol percent.

EXAMPLE 14

Into a reaction flask there were added:
0.40 grams (2 mmols) of cupric acetate monohydrate,
0.36 grams (4 mmols) of N-methyl glycine, and 50 ml of ion exchanged water.

Into a 500 ml creased Morton flask fitted with a gas addition tube, a condenser, a thermometer, and a stirrer capable of operating at speeds in the range of from about 8,000 to about 10,000 rpm, there were added:

48.8 grams (400 mmols) of 2,6-xylenol,
0.2 grams of Ultrawet K soft, sodium dodecyl benzene sulfonate, and
150 ml of ion exchanged water.

To the resulting solution there was added the catalyst composition prepared above. The resulting mixture was stirred under oxygen and heated to a temperature of 55° C. There was then added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 25° C.

The reaction mixture was filtered and washed with water. A sample of the solid was removed, dissolved in acetone and analyzed by gas-liquid chromatography. The analysis indicated that 23 mol percent of the 2,6-xylenol was unreacted.

The solid was air dried and washed twice with 200 ml of benzene to remove 2,6-xylenol and polyphenoxy ether. The resulting yellow solid was dried at 60° C. Analysis of the product indicated a yield of tetramethylbiphenol equal to 58.2 mol percent.

EXAMPLE 15

Into a reaction flask there were added:
0.40 grams (2 mmols) of cupric acetate monohydrate,
0.47 grams (4 mmols) of N-acetyl glycine, and
50 ml of ion exchanged water.

Into a 500 ml creased Morton flask fitted with a gas addition tube, a condenser, a thermometer, and a stirrer capable of operating at speeds in the range of from about 8,000 to about 10,000 rpm, there were added:

48.8 grams (400 mmols) of 2,6-xylenol,
0.2 grams of Ultrawet K soft, sodium dodecyl benzene sulfonate, and
200 ml of ion exchanged water.

To the resulting solution there was added 100 ml of the catalyst composition prepared above. The resulting mixture was stirred under oxygen and heated to a temperature of 57° C. at which time there was added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered, and the solid was washed with water, dilute HCl and again with water. A sample of the solid was removed, dissolved in acetone and analyzed by gas-liquid chromatography. A sample of an oil removed in the first water wash was extracted with methylene chloride and analyzed by gas-liquid chromatography. The analysis indicated that 23.3 mol percent of the 2,6-xylenol was unreacted.

The solid was air dried and washed twice with 100 ml of benzene to remove 2,6-xylenol and polyphenoxy ether. The resulting yellow solid was dried at 60° C. Analysis of the product indicated a yield of tetramethylbiphenol equal to 3 mol percent.

EXAMPLE 16

Into a reaction flask there were added:
0.40 grams (2 mmols) of cupric acetate monohydrate,
0.55 grams (4 mmols) of N-phenylglycine, and
25 ml of ion exchanged water.

Into a 500 ml creased Morton flask fitted with a gas addition tube, a condenser, a thermometer, and a stirrer capable of operating at speeds in the range of from about 8,000 to about 10,000 rpm, there were added:

48.8 grams (400 mmols) of 2,6-xylenol,
0.2 grams of Ultrawet K soft, and
200 ml of ion exchanged water.

To the resulting solution there was added the catalyst composition prepared above. The resulting mixture was stirred under oxygen and heated to a temperature of 50° C. At that time there was added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered, the solids air dried, a sample of the solid was removed, dissolved in acetone and analyzed by gas-liquid chromatography. The analysis indicated that 5 mol percent of the 2,6-xylenol was unreacted.

The dry solid was washed twice with 200 ml of benzene to remove 2,6-xylenol and polyphenoxy ether. The resulting light yellow solid was dried at 60° C. Analysis of the product indicated a yield of tetramethylbiphenol equal to 61 mol percent.

EXAMPLE 17

Into a reaction flask there were added:
0.40 grams (2 mmols) of cupric acetate monohydrate,
0.53 grams (4 mmols) of glycylglycine, and 50 ml of ion exchanged water.

Into a 500 ml creased Morton flask fitted with a gas addition tube, a condenser, a thermometer, and a stirrer capable of operating at speeds in the range of from about 8,000 to about 10,000 rpm, there were added:

48.8 grams (400 mmols) of 2,6-xylenol,
0.2 grams of Ultrawet K soft, and 200 ml of ion exchanged water.

To the resulting solution there was added the catalyst composition prepared above. The resulting mixture was stirred under oxygen and heated to a temperature of 52° C. At this temperature there was added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the solids were washed with water. Analysis of the oil phase remaining in the filtrate indicated that 27 mol percent of the 2,6-xylenol was unreacted.

The solid was air dried and washed twice with 100 ml of benzene to remove 2,6-xylenol and polyphenoxy ether. The resulting yellow solid was dried at 60° C. Analysis of the product indicated a yield of tetramethylbiphenol equal to 35.2 mol percent.

EXAMPLE 18

Into a reaction flask there were added:
0.40 grams (2 mmols) of cupric acetate monohydrate,
1.28 grams (4 mmols) of glutathione, and 25 ml of ion exchanged water.

To the resulting mixture there was added 4.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
  48.8 grams (400 mmols) of 2,6-xylenol,
  0.2 grams of sodium dodecyl benzene sulfonate, and
  200 ml of ion exchanged water.

To the resulting solution there was added the catalyst composition prepared above. The resulting mixture was stirred under oxygen and heated to a temperature of 57° C. at which time there was added 4.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the filtrate was treated with hydrochloric acid and refiltered. The solid fraction was washed with water. A sample of the solid was removed, dissolved in acetone and analyzed by gas-liquid chromatography. The analysis indicated that 59.6 mol percent of the 2,6-xylenol was unreacted.

The solid was air dried and washed twice with 200 ml of benzene to remove 2,6-xylenol and polyphenoxy ether. The resulting yellow solid was dried at 60° C. Analysis of the product indicated a yield of tetramethylbiphenol equal to 20.7 percent.

EXAMPLE 19

Into a reaction flask there were added:
  0.40 grams (2 mmols) of cupric acetate monohydrate,
  0.36 grams (4 mmols) of β-alanine, and
  50 ml of ion exchanged water.

Into a 500 ml creased flank fitted with a gas addition tube, a condenser, a thermometer, and a stirrer capable of operating at speeds in the range of from about 8,000 to about 10,000 rpm, there were added:
  48.8 grams (400 mmols) of 2,6-xylenol,
  0.2 grams of Ultrawet K soft, medium dodecyl benzene sulfonate, and
  200 ml of ion exchanged water.

To the resulting solution there was added 100 ml of the catalyst composition prepared above. The resulting mixture was stirred under oxygen and heated to a temperature of 50° C. There was added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the solids washed with water. A sample of the solid was removed, dissolved in acetone and analyzed by gas-liquid chromatography. The analysis indicated that 11 mol percent of the 2,6-xylenol was unreacted. The solid was air dried and washed twice with 100 ml of benzene to remove 2,6-xylenol and polyphenoxy ether. The resulting light yellow solid was dried at 60° C. Analysis of the product indicated a yield of tetramethylbiphenol equal to 62 mol percent.

EXAMPLE 20

Into a reaction flask there were added:
  0.40 grams (2 mmols) of cupric acetate monohydrate,
  0.41 grams (4 mmols) of 3-amino butyric acid, and 25 ml of ion exchanged water.

Into a 500 ml creased Morton flask fitted with a gas addition tube, a condenser, a thermometer, and a stirrer capable of operating at speeds in the range of from about 8,000 to about 10,000 rpm, there were added:
  48.8 grams (400 mmols) of 2,6-xylenol,
  0.2 grams of Ultrawet K soft, sodium dodecyl benzene sulfonate, and
  200 ml of ion exchanged water.

To the resulting solution there was added 100 ml of the catalyst composition prepared above. The resulting mixture was stirred under oxygen and heated to a temperature of 50° C. at which time there was added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered, the solid was washed with water, and removed, dissolved in acetone and analyzed by gas-liquid chromatography. The analysis indicated that all of the 2,6-xylenol had reacted.

The solid was air dried and washed twice with 200 ml of benzene to remove 2,6-xylenol and polyphenoxy ether. The resulting yellow solid was dried at 60° C. Analysis of the product indicated a yield of tetramethylbiphenol equal to 66.3 mol percent.

EXAMPLE 21

Into a 500 ml creased Morton flask fitted with a gas addition tube, a condenser, a thermometer, and a stirrer capable of operating at speeds in the range of from about 8,000 to about 10,000 rpm, there were added:
  65.7 grams (400 mmols) of 2-methyl-6-t-butyl phenol,
  0.2 grams of sodium lauryl sulfate, and 150 ml of ion exchanged water. The resulting mixture was stirred and there was added:
  0.25 grams of cupric glycinate in
  50 ml of ion exchanged water. After stirring for 5 minutes there was added:
  10 ml of a 1.0 Normal solution of sodium bicarbonate and the resulting mixture was stirred for an additional 5 minutes. The reaction mixture was then heated to a temperature of 90° C. and a slow stream of oxygen was introduced. At the end of 6 hrs., the reaction was flushed with nitrogen and cooled to a temperature of 20° C.

The reaction mixture was filtered, a sample of the solid was removed, dissolved in acetone and analyzed by gasliquid chromatography. The analysis indicated that all of the methyl-t-butyl phenol had reacted.

The solid was air dried and hydrogenated in methanol in the presence of palladium or carbon to yield the biphenol having a melting point of from 184° C.–185° C.

EXAMPLE 22

Into a 500 ml creased Morton flask fitted with a gas addition tube, a condenser, a thermometer, and a stirrer capable of operating at speeds in the range of from about 8,000 to about 10,000 rpm, there were added:
  71.3 grams (400 mmols) of 2,6-diisopropylphenol,
  0.2 grams of sodium lauryl sulfate, and
  150 ml of ion exchanged water. There was then added:
  0.25 grams of cupric glycinate in
  25 ml of ion exchanged water. The reaction mixture was stirred for 5 minutes and there was then added:
  10 ml of a 1.0 Normal solution of sodium bicarbonate. The reaction mixture was then heated to a temperature of 90° C. and a slow stream of oxygen was introduced.

At the end of 6 hrs., the reaction was flushed with nitrogen and cooled to a temperature of 20° C.

The reaction mixture was filtered, a sample of the solid was removed, dissolved in acetone and analyzed by gas-liquid chromatography. The analysis indicated that all of the 2,6-diisopropylphenol had reacted.

The solid was washed with water and the resulting red solid was air dried yielding 68 grams of product having a melting point of 197°–199° C. This corresponded to a 97 mol percent conversion to the tetra isopropyl diphenoquinone.

EXAMPLE 23

Into a first flask there were added:
0.20 grams (1 mmol) of cupric acetate monohydrate,
0.15 grams (2 mmols) of glycine, and
30 ml of ion exchanged water.

Into a 500 ml creased Morton flask, fitted with a gas addition tube, a condenser, a thermometer, and a stirrer capable of operating at speeds in the range of from about 8,000 to about 10,000 rpm, there were added:
82.3 grams (400 mmols) of 2,4-ditertiarybutylphenol,
0.20 grams of sodium lauryl sulfate, and
120 ml of ion exchanged water.

To the resulting mixture there was added the copper/glycine composition prepared above. The resulting mixture was stirred under oxygen for 15 minutes and there was then added 12.0 ml of a 1.0 Normal sodium bicarbonate solution.

The reaction mixture was heated to a temperature of 80° C. and a slow stream of oxygen was introduced. After 2 ½ hours a sample was removed and analyzed by gas-liquid chromatography the results of which indicated that all of the phenol had reacted. After an additional 10 minutes, the reaction was flushed with nitrogen and cooled to a temperature of 20° C.

The reaction mixture was filtered and the solids were blended with cold water, filtered, washed with 400 ml of dilute HCl and washed with water until neutral. The resulting solids were dried at 60° C. and purified as follows.

76 grams of the solids were stirred with 400 ml of acetone and heated to reflux resulting in a clear solution. Acetone was distilled off to the cloud point and the mixture was cooled to room temperature, filtered and the solids were washed with methanol. The solids were dried at 60° C. resulting in 39.2 grams of white crystals having a melting point of 196.5° C. and identified as the 3,3',5,5'-tetratertiarybutyl-2,2'-dihydroxy diphenyl.

EXAMPLE 24

Into a first flask there were added:
0.20 grams (1 mmol) of cupric acetate monohydrate,
0.15 grams (2 mmols) of glycine, and
30 ml of ion exchanged water.

Into a 500 ml creased Morton flask, fitted with a gas addition tube, a condenser, a thermometer, and a stirrer capable of operating at speeds in the range of from about 8,000 to about 10,000 rpm, there were added:
65.2 grams (400 mmols) of 2-methyl-4-tertiarybutylphenol,
0.2 grams of sodium lauryl sulfate, and
150 ml of ion exchanged water.

To the resulting mixture there was added the copper/glycine composition prepared above. The resulting mixture was stirred for 15 min. and there was then added 12.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the solids treated with 200 ml of methanol. The remaining bright yellow solid weighed 14.1 grams, had a melting point of 215°–218° C. and was identified as a mixture of the o,o'-biphenol and the o,o'-diphenoquinone.

EXAMPLE 25

Into a first flask there were added:
0.49 grams (2 mmols) of manganous acetate tetrahydrate,
0.30 grams (4 mmols) of glycine, and
30 ml of ion exchanged water.

Into a 500 ml creased Morton flask, fitted with a gas addition tube, a condenser, a thermometer, and a stirrer capable of operating at speeds in the range of from about 8,000 to about 10,000 rpm, there were added:
48.8 grams (400 mmols) of 2,6-xylenol,
0.2 grams of sodium lauryl sulfate, and
130 ml of ion exchanged water.

To the resulting mixture there was added the manganese/glycine composition prepared above. The resulting mixture was stirred for 15 minutes and there was then added 16.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the solids washed with water and dried.

The dried solid weighing 33.1 grams was washed twice with 150 ml of benzene to remove any 2,6-xylenol and polyphenoxy ether. The resulting solid was dried at 60° C. Analysis of the product indicated a yield of tetramethylbiphenol equal to 22.8 mol percent.

EXAMPLE 26

Into a first flask there were added:
0.50 grams (2 mmols) of nickel acetate tetrahydrate (Ni(OAC)$_2$4H$_2$O)
3.30 grams (4 mmols) of glycine, and
30 ml of ion exchanged water.

Into a 500 ml creased Morton flask, fitted with a gas addition tube, a condenser, a thermometer, and a stirrer capable of operating at speeds in the range of from about 8,000 to about 10,000 rpm, there were added:
48.8 grams (400 mmols) of 2,6-xylenol,
0.2 grams of sodium lauryl sulfate, and
130 ml of ion exchanged water.

To the resulting slurry there was added the nickel/glycine composition prepared above. The resulting mixture was stirred for 0.5-min. and there was then added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the solids washed with water and dried.

The dried solid, weighing 22.8 grams was washed twice with 100 ml of benzene to remove 2,6-xylenol and polyphenoxy ether. The resulting solid was dried at 60° C. Analysis of the product indicated a yield of tetramethylbiphenol equal to 31.5 mol percent.

EXAMPLE 27

Into a 500 ml creased Morton flask, fitted with a gas addition tube, a condenser, a thermometer, and a stirrer capable of operating at speeds in the range of from about 8,000 to about 10,000 rpm, there were added:
- 48.8 grams (400 mmols) of 2,6-xylenol, and
- 300 ml of ion exchanged water.

The resulting mixture was stirred and heated to 50° C. at which time there was added 5 grams of cuprice glycinate. The reaction mixture was heated to 80° C. and a slow stream of oxygen was introduced. At the end of 6 hrs., the reaction was flushed with nitrogen and cooled to a temperature of 20° C. The reaction mixture was filtered and the solids washed with water. The solids were then air dried and washed twice with 100 ml of benzene to remove 2,6-xylenol and polyphenoxy ether. The resulting solid was dried at 60° C. Analysis of the product indicated a yield of tetramethylbiphenol equal to 33.5 mol percent.

EXAMPLE 28

Into a first flask there were added:
- 0.50 grams (2 soft. mmols) of cobalt acetate tetrahydrate,
- 0.30 grams (4 mmols) of glycine, and
- 40 ml of ion exchanged water.

To the resulting mixture there was added 39.2 ml of a 0.1028 Normal solution of potassium hydroxide. The potassium hydroxide solution was added drop-wise and the total amount added was equal to 4.03 ml equivalents of potassium hydroxide. The resulting mixture, which had a pH of 8.3, was bottled and stored.

Into a 500 ml creased Morton flask fitted with a gas addition tube, condenser, thermometer, and a stirrer capable of operating at speeds in the range of from about 8,000 to about 10,000 rpm, there were added:
- 48.8 grams (400 mmols) of 2,6-xylenol,
- 185 ml of ion exchanged water,
- 0.2 grams of Ultrawet K soft, and
- 65 ml of the metal complex prepared above.

The resulting reaction mixture was heated to 53° C. at which time there was added 4.0 ml of a 1.0 Normal sodium bicarbonate solution. The reaction mixture was then heated to a temperature of 80° C. and a slow stream of oxygen was introduced. At the end of 6 hrs., the reaction was flushed with nitrogen and cooled to a temperature of 20° C.

The reaction mixture was filtered and a sample of the solid removed, dissovled in acetone and analyzed by gas-liquid chromatography. The analysis indicated that 72 percent of the 2,6-xylenol had reacted. The solid was air dried and washed twice with 50 ml of benzene to remove 2,6-xylenol and polyphenoxy ether. The resulting solid was dried at 60° C. resulting in 15 grams of a light yellow solid having a melting point of 222° C. The results indicated a yield of tetramethylbiphenol equal to 31 mol percent.

EXAMPLE 29

Into a reaction flask there were added:
- 0.50 grams (2 mmols) of cobalt acetate tetrahydrate,
- 0.30 grams (4 mmols) of glycine, and
- 40 ml of ion exchanged water.

To the resulting slurry there was added 4.0 ml of a 1.0 Normal solution of sodium bicarbonate.

Into a 500 ml creased Morton flask fitted with a gas addition tube, a condenser, a thermometer, and a stirrer capable of operating at speeds in the range of from about 8,000 to about 10,000 rpm, there were added:
- 48.8 grams (400 mmols) of 2,6-xylenol,
- 200 ml of ion exchanged water, and
- 0.2-grams of Ultrawet K soft.1

To the resulting mixture there was added the metal complex prepared above and the reaction mixture was then heated to 80° C. When this temperature was reached there was added 4.0 ml of a 1.0 Normal sodium bicarbonate solution. The reaction mixture was maintained at 80° C. and a slow stream of oxygen introduced for 6 hrs. At the end of this time, the reaction was flushed with nitrogen and cooled to a temperature of 20° C.

The reaction mixture was filtered and a sample of the solid was removed, dissolved in acetone, and analyzed by gas-liquid chromatography. The analysis indicated that 53 percent of the 2,6-xylenol had reacted.

The solid was air dried and washed twice with 100 ml of benzene to remove 2,6-xylenol and polyphenoxy ether. The resulting solid was dried at 60° C. to yield 12 grams of product having a melting point of 224° C. These results indicated a yield of tetramethylbiphenol equal to 25 mol percent.

EXAMPLE 30

Into a 500 ml creased Morton flask, fitted with a gas addition tube, a condenser, a thermometer, and a stirrer capable of operating at speeds in the range of from about 8,000 to about 10,000 rpm there were added:
- 31.2 grams (200 mmols) of 2,6-dimethoxyphenol,
- 0.10 grams (0.3 mmol) of sodium lauryl sulfate, and
- 170 ml of ion exchanged water.

The resulting reaction mixture was stirred and there was added a mixture comprising:
- 0.20 grams (1 mmol) of cupric acetate monohydrate,
- 0.15 grams (2 mmols) of glycine, and
- 30 ml of ion exchanged water.

The resulting reaction mixture was stirred under oxygen and heated to a temperature of 80° C. and maintained at that temperature for 2 hrs. At the end of this time the heat and oxygen were discontinued and the reaction mixture allowed to cool to room temperature. The reaction mixture was filtered and the purple solids were washed with water. A sample of the solids analyzed by gas liquid chromatography indicated that 93 percent of the dimethoxyphenol had reacted. The solid was washed with xylene to remove any unreacted dimethoxyphenol and dried at 60° C. The dried product weighed 16.9 grams and infrared analysis indicated that the material was the tetramethoxy diphenoquinone. The yield of product was equal to 55 mol percent.

EXAMPLE 31

Into a 500 ml creased Morton flask, fitted with a gas addition tube, a condenser, a thermometer, and a stirrer capable of operating at speeds in the range of from about 8,000 to about 10,000 rpm there were added:
- 43.3 grams (300 mmols) of 1-naphthol, 0.20 gram (0.6 mmol) of sodium lauryl sulfate, and
- 190 ml of ion exchanged water.

The resulting reaction mixture was stirred and there was added a mixture comprising:
- 0.10-gram (0.5mmol) of cupric acetate monohydrate,
- 0.08 gram (1 mmol) of glycine, and
- 30 ml of ion exchanged water.

The mixture was stirred for 15 minutes and there was then added 16 ml of a 1.0 Normal solution of sodium bicarbonate.

The resulting reaction mixture was stirred under oxygen and heated to a temperature of 90° C. and maintained at a temperature of from 90°–95° C. for 5 hrs., during which time oxygen was continuously introduced. At the end of this time the heat and oxygen were discontinued and the reaction mixture cooled to 25° C.

The reaction mixture was filtered resulting in a clear, red filtrate which had a pH of 8.7. The filtrate was acidified with HCl to a pH of 2 and again filtered to remove solids. The filtrate was discarded and the solids were washed with 209 ml of water and air dried. A sample of the solid was removed and analyzed by gas-liquid chromatography. The analysis indicated that all of the 1-naphthol had reacted.

The solid was air dried and washed twice with 150 ml of xylene. The resulting solid wad dried at 60° C. to yield 39.2 grams of a dark brown solid. Infrared analysis indicated a yield of carbon-carbon coupled products equal to 90.7 mol percent consisting of 1 part of the naphthenoquinone and 2–3 parts of the binaphthol.

EXAMPLE 32

Into a 500 ml creased Morton flask, fitted with a gas addition tube, a condenser, a thermometer, and a stirrer capable of operating at speeds in the range of from about 8,000 to about 10,000 rpm there were added:
  55.4 grams (400 mmols) of 2,4,6-trimethylphenol (98.3%,
  0.20 gram (0.6 mmol) of sodium lauryl sulfate, and
  150 ml of ion exhanged water.

The resulting reaction mixture was stirred and there was added a mixture comprising:
  0.40 gram (2 mmols) of cupric acetate monohydrate,
  0.30 gram (4 mmols) of glycine, and
  25-ml of ion exchanged water.

The mixture was stirred for 5 minutes and there was then added 20 ml of a 1.0 Normal solution of sodium bicarbonate.

The resulting reaction mixture was stirred under oxygen and heated to a temperature of 80° C. and maintained at that temperature for 6 hrs. During this time the pH of the reaction mixture was checked and maintained at between 9.0 and 9.4 by the addition of solid sodium hydroxide pellets. The total amount of NaOH added during the course of the reaction was equal to 16.2 grams. At the end of this time the heat and oxygen were discontinued and the reaction mixture cooled to 25° C.

The reaction mixture was filtered to separate a solid product and a dark red filtrate which was acidified with 37 ml of concentrated HCl to precipitate a brown-red solid. This solid fraction was washed with 100 ml of xylene and dried at 60° C. to yield 8.33 grams of a brown solid. The first solid fraction removed by the original filtration was washed with water, air dried and washed with 150 ml of xylene. After this it was dried at 60° C. to yield 12.73 grams of a brown solid. Total yield of product was equal to 38 mol percent. Infrared analysis of the product indicated a mixture of the following two materials:

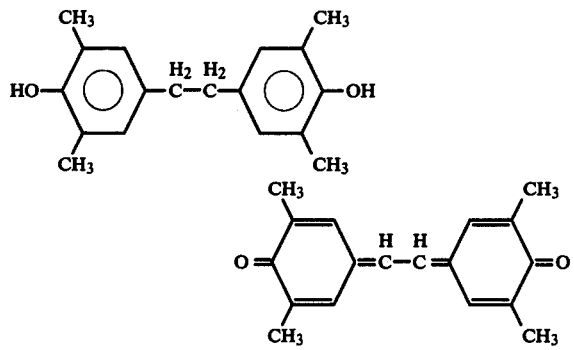

What is claimed is:

1. A catalyst composition comprising:
   (a) a metal complex of an aminocarboxylic acid or an aminosulfonic acid wherein the metal is selected from the group consisting of cupric, cobaltous, manganous and nickelous ions, said metal complex being the product obtained by reacting a source of the metal ion with an aminocarboxylic or an aminosulfonic acid, and
   alkaline material selected from the group consisting of alkali metal hydroxides, alkali metal carbonates and alkali metal bicarbonates.

2. A catalyst composition, as claimed in claim 1, wherein the metal complex is a cupric complex of an aminocarboxylic acid.

3. A catalyst composition, as claimed in claim 1, wherein the aminocarboxylic is an alpha aminocarboxylic acid.

4. A catalyst composition, as claimed in claim 3, wherein the aminocarboxylic acid is glycine.

5. A catalyst composition, as claimed in claim 1, wherein the alkaline material is an alkali metal bicarbonate.

* * * * *

UNITED STATES PATENT AND TRADEMARK OFFICE
CERTIFICATE OF CORRECTION

PATENT NO. : 4,147,663
DATED : April 3, 1979
INVENTOR(S) : Thomas F. Rutledge

It is certified that error appears in the above-identified patent and that said Letters Patent are hereby corrected as shown below:

Column 5, line 49 "and" should read -- are --

Column 9, line 63 "  CH$_2$- " should read --  CH$_2$— --

Column 10, line 4 "NH" should read -- NH$_2$ --

Column 13, lines 13 & 14 "phenol naphthol." should read -- phenol or naphthol. --

Column 14, line 32 "oxidably" should read -- oxidative --

Column 15, line 29 "oleyl, alcohol " should read -- oleyl alcohol

Column 15, line 30 "dieleate" should read -- dioleate --

Column 17, line 4 "about carbon" should read -- about 6 carbon --

Column 34, line 37 "alkaline" should read -- (b) an alkaline --

Signed and Sealed this

Eighth Day of January 1980

[SEAL]

Attest:

SIDNEY A. DIAMOND

Attesting Officer

Commissioner of Patents and Trademarks